US012653511B2

(12) United States Patent
Cant et al.

(10) Patent No.: US 12,653,511 B2
(45) Date of Patent: Jun. 16, 2026

(54) SYSTEM FOR PROTECTING A TISSUE SPECIMEN

(71) Applicants:Joseph Richard Cant, Naples, FL (US); Gary Michael Wilson, Naples, FL (US)

(72) Inventors: Joseph Richard Cant, Naples, FL (US); Gary Michael Wilson, Naples, FL (US)

( * ) Notice: Subject to any disclaimer, the term of this patent is extended or adjusted under 35 U.S.C. 154(b) by 0 days.

(21) Appl. No.: 18/806,884

(22) Filed: Aug. 16, 2024

(65) Prior Publication Data

US 2025/0057513 A1 Feb. 20, 2025

Related U.S. Application Data

(60) Provisional application No. 63/520,490, filed on Aug. 18, 2023.

(51) Int. Cl.
*A61B 10/02* (2006.01)
(52) U.S. Cl.
CPC .................................... *A61B 10/02* (2013.01)
(58) Field of Classification Search
CPC .... A61B 10/02; A61B 19/02; B65D 25/2873; B65D 2525/285; B65D 57/00
USPC ............. 206/438–440, 447, 484–484.2, 497, 206/557–565
See application file for complete search history.

(56) References Cited

U.S. PATENT DOCUMENTS

| | | | |
|---|---|---|---|
| 1,461,689 A * | 7/1923 | Swanson ............ | B65D 25/2873 206/447 |
| 3,203,870 A | 8/1965 | Andelin | |
| 4,105,116 A | 8/1978 | Jones et al. | |
| 4,482,053 A | 11/1984 | Alpern et al. | |
| 4,557,903 A * | 12/1985 | McCormick ............. | G01N 1/36 206/439 |
| 5,056,930 A * | 10/1991 | Mestetsky .............. | B65D 33/20 383/66 |

(Continued)

FOREIGN PATENT DOCUMENTS

| | | |
|---|---|---|
| CN | 2491818 Y | 5/2002 |
| CN | 202024921 U | 11/2011 |

(Continued)

OTHER PUBLICATIONS

English language abstract for CN 2491818 Y extracted from espacenet. com database on Aug. 16, 2024, 1 page.

(Continued)

*Primary Examiner* — Bryon P Gehman
(74) *Attorney, Agent, or Firm* — Howard & Howard Attorneys PLLC

(57) ABSTRACT

The subject disclosure provides for a system for protecting a tissue specimen. The system also includes a tray having a base with a surface portion for supporting the tissue specimen and a receiver portion, and a spacer with a body portion and a securing portion engaging the receiver portion of the base to position the body portion above the surface portion of the base. The system also includes a sterile container having a top and a bottom defining a cavity with the tray positionable within the cavity such that the body portion of the spacer engages the top of the sterile container to elevate the top of the sterile container away from the surface portion of the base for protecting the tissue specimen from contamination.

19 Claims, 11 Drawing Sheets

(56)          References Cited

U.S. PATENT DOCUMENTS

| | | | |
|---|---|---|---|
| 5,080,225 | A | 1/1992 | Russo et al. |
| 5,115,913 | A * | 5/1992 | Anhauser ............... B65D 75/54 |
| | | | 206/440 |
| 5,257,692 | A | 11/1993 | Heacox |
| 5,816,403 | A | 10/1998 | Wilkes et al. |
| 5,854,065 | A | 12/1998 | Livingston et al. |
| 6,337,052 | B1 * | 1/2002 | Rosenwasser ..... B65D 81/3834 |
| | | | 206/438 |
| 6,602,704 | B1 | 8/2003 | Maxwell et al. |
| 6,622,865 | B1 * | 9/2003 | Theobald ............... B65D 75/54 |
| | | | 206/447 |
| 7,316,318 | B1 | 1/2008 | Rosten et al. |
| 8,113,348 | B2 | 2/2012 | Foster |
| 10,288,531 | B2 | 5/2019 | Giles |
| 2005/0160701 | A1 | 7/2005 | Stevens |
| 2005/0189362 | A1 | 9/2005 | Muller |
| 2008/0237228 | A1 | 10/2008 | Chou |
| 2018/0078665 | A1 | 3/2018 | Buccellato |
| 2022/0330542 | A1 | 10/2022 | Koepsel et al. |

FOREIGN PATENT DOCUMENTS

| | | |
|---|---|---|
| CN | 202974738 U | 6/2013 |
| WO | 9937233 A1 | 7/1999 |

OTHER PUBLICATIONS

English language abstract for CN 202024921 U extracted from espacenet.com database on Aug. 16, 2024, 1 page.
English language abstract for CN 202974738 U extracted from espacenet.com database on Aug. 16, 2024, 1 page.

* cited by examiner

SYSTEM FOR PROTECTING A TISSUE SPECIMEN

CROSS-REFERENCE TO RELATED APPLICATIONS

The subject application claims priority to and all the benefits of U.S. Provisional Patent Application No. 63/520, 490, filed Aug. 18, 2023, the disclosure of which is incorporated by reference in its entirety herein.

FIELD OF DISCLOSURE

The subject disclosure generally relates to a system for protecting a tissue specimen.

BACKGROUND

Tissue specimens used in medical and research settings are susceptible to contamination during handling and transportation. Contaminants can compromise the specimen's integrity, affecting diagnostic accuracy and research outcomes. Therefore, there is a need for a system that can protect tissue specimens from contamination while maintaining their sterility.

SUMMARY

The subject disclosure provides for a system for protecting a tissue specimen. The system also includes a tray having a base with a surface portion for supporting the tissue specimen and a receiver portion, and a spacer with a body portion and a securing portion engaging the receiver portion of the base to position the body portion above the surface portion of the base. The system also includes a sterile container having a top and a bottom defining a cavity with the tray positionable within the cavity such that the body portion of the spacer engages the top of the sterile container to elevate the top of the sterile container away from the surface portion of the base for protecting the tissue specimen from contamination.

The subject disclosure also provides for a method of protecting a tissue specimen using a tray having a base and a spacer. The method also includes placing the tissue specimen onto the base, securing the spacer onto the base such that a portion of the spacer is positioned above the base, and positioning the tray into the sterile container such that the spacer elevates the sterile container away from the base of the tray to protect the tissue specimen from contamination.

The subject disclosure also provides a tray for use with a sterile container to protect a tissue specimen. The tray includes a base with a surface portion and a receiver portion, and a spacer with a body portion and a securing portion engaging the receiver portion of the base to position the body portion above said surface portion of the base, and where the body portion of the spacer remains positioned above the surface portion of the base for continuously protecting the tissue specimen as the tray is positioned within the sterile container.

BRIEF DESCRIPTION OF THE DRAWINGS

Advantages of the present invention will be readily appreciated as the same becomes better understood by reference to the following detailed description when considered in connection with the accompanying drawings.

DETAILED DESCRIPTION

Referring to the Figures, wherein like numerals indicate like or corresponding components throughout the several views, a system 10 for protecting a tissue specimen 18 (which may also be known as a tissue sample) is shown.

Figure 1:
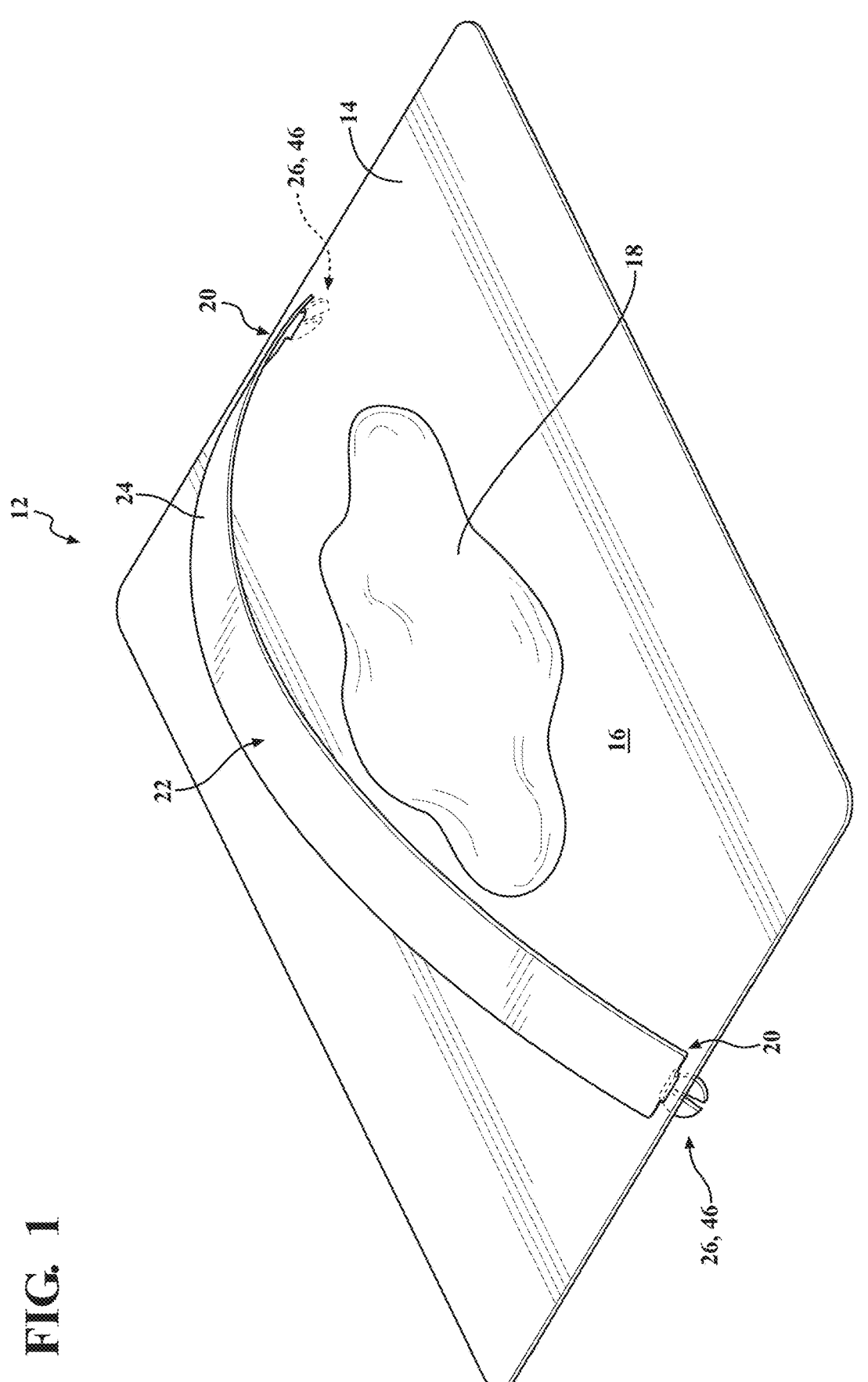
FIG. 1 is a perspective view of a tray supporting a tissue specimen including a base and a spacer.
Figure 2:
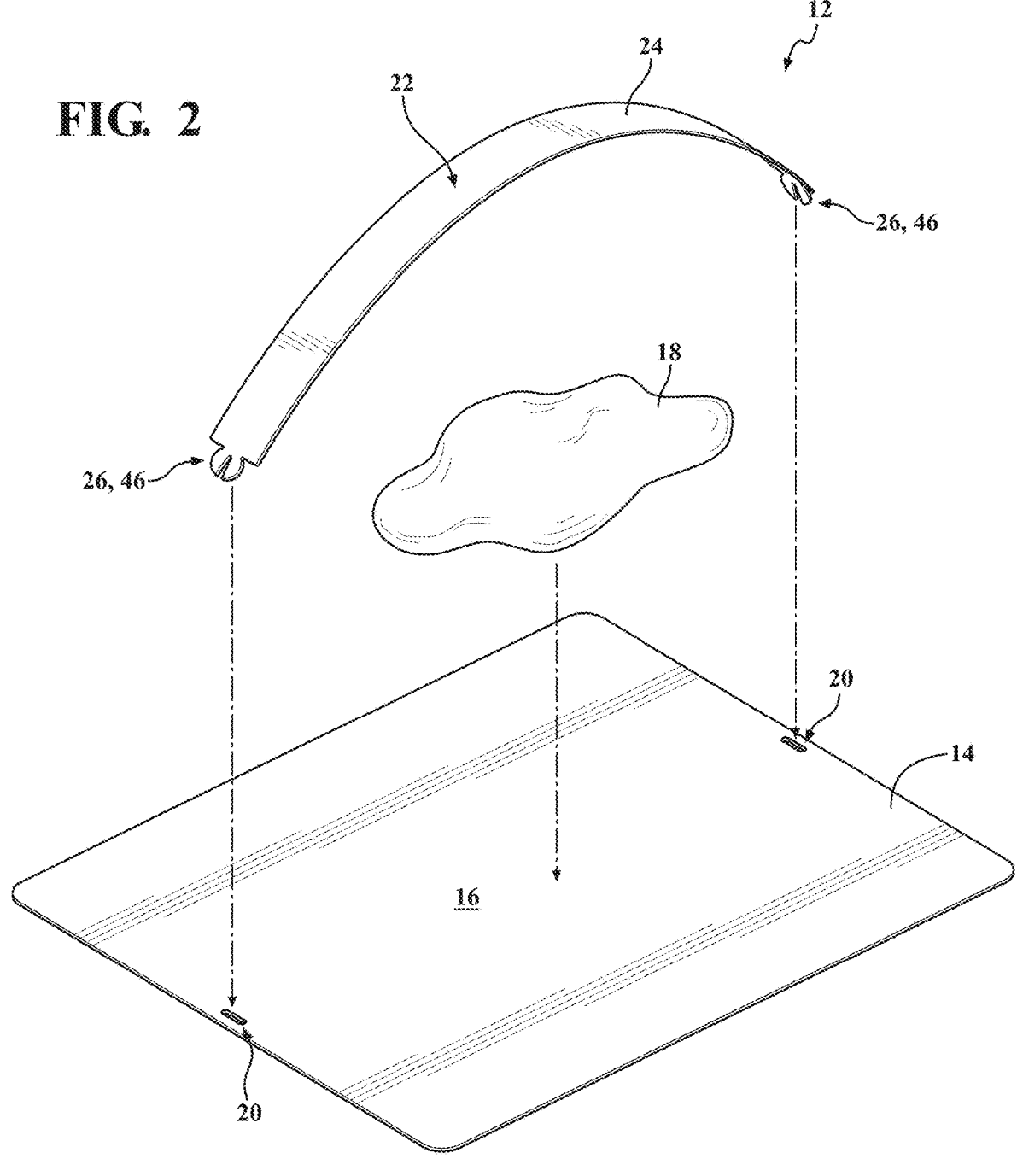
FIG. 2 is an exploded perspective view of the tray supporting the tissue specimen.
Figure 3:
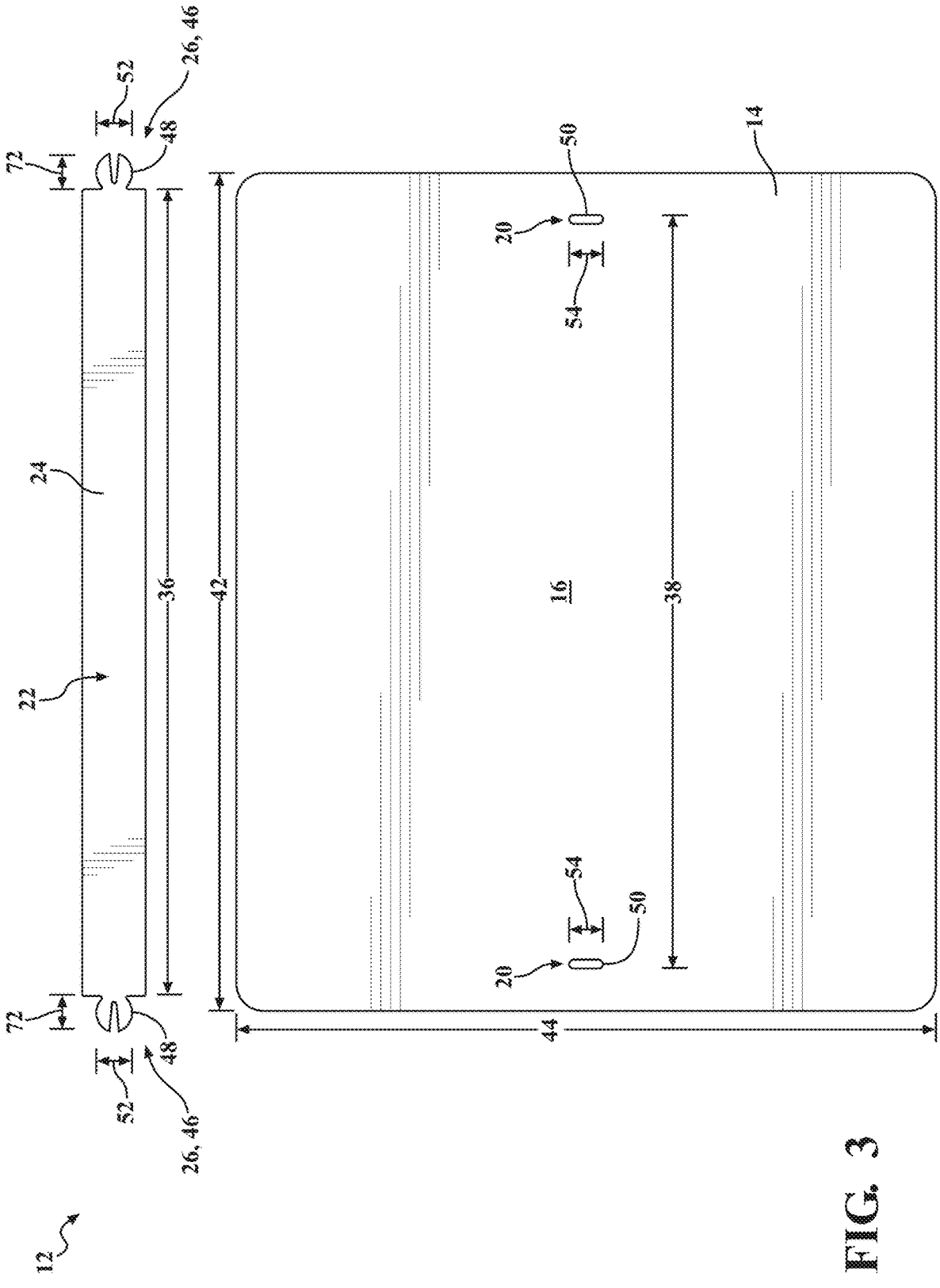
FIG. 3 is a plan view of the base and the spacer of the tray.
Figure 4:
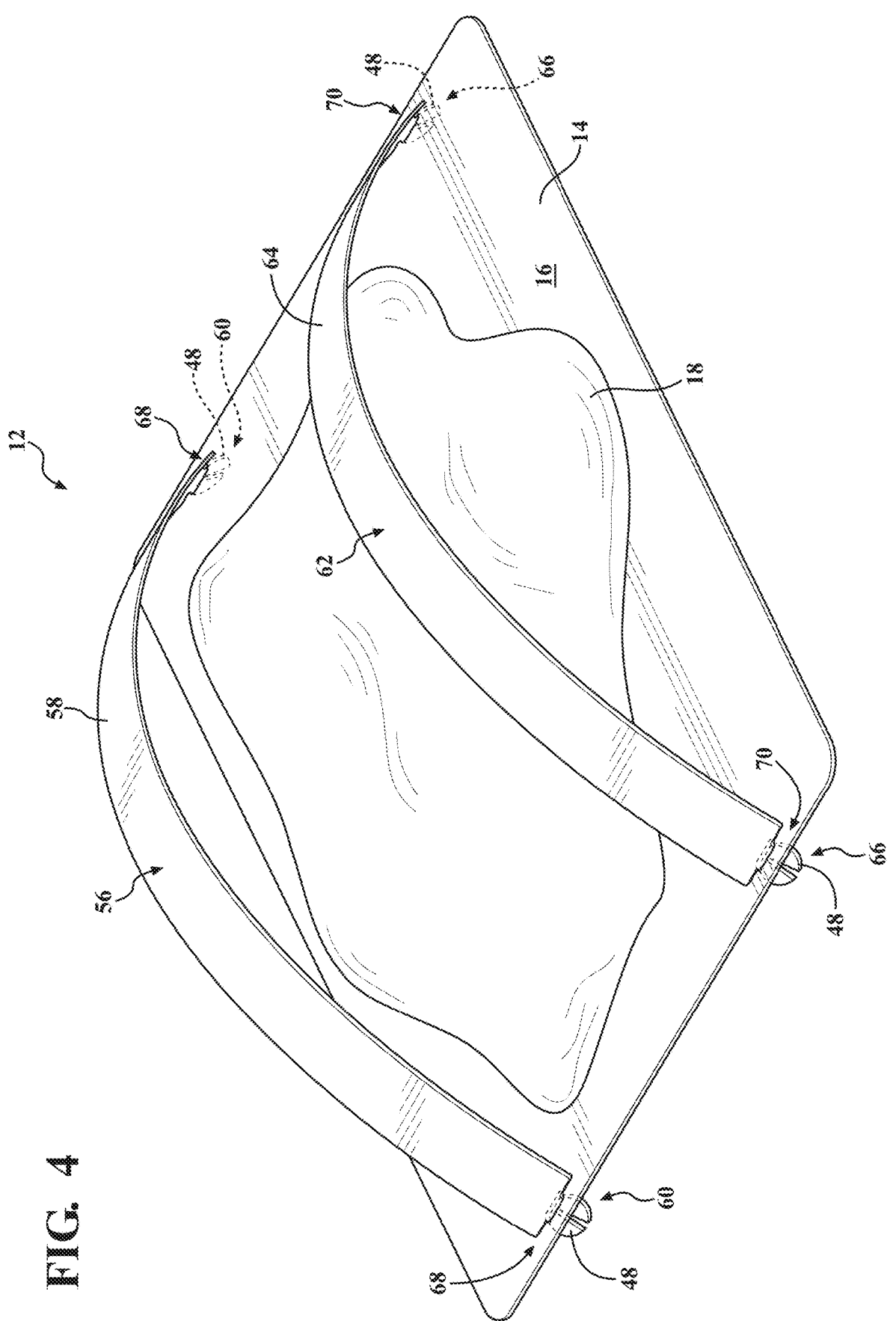
FIG. 4 is a perspective view of a tray including two spacers.
Figure 5:
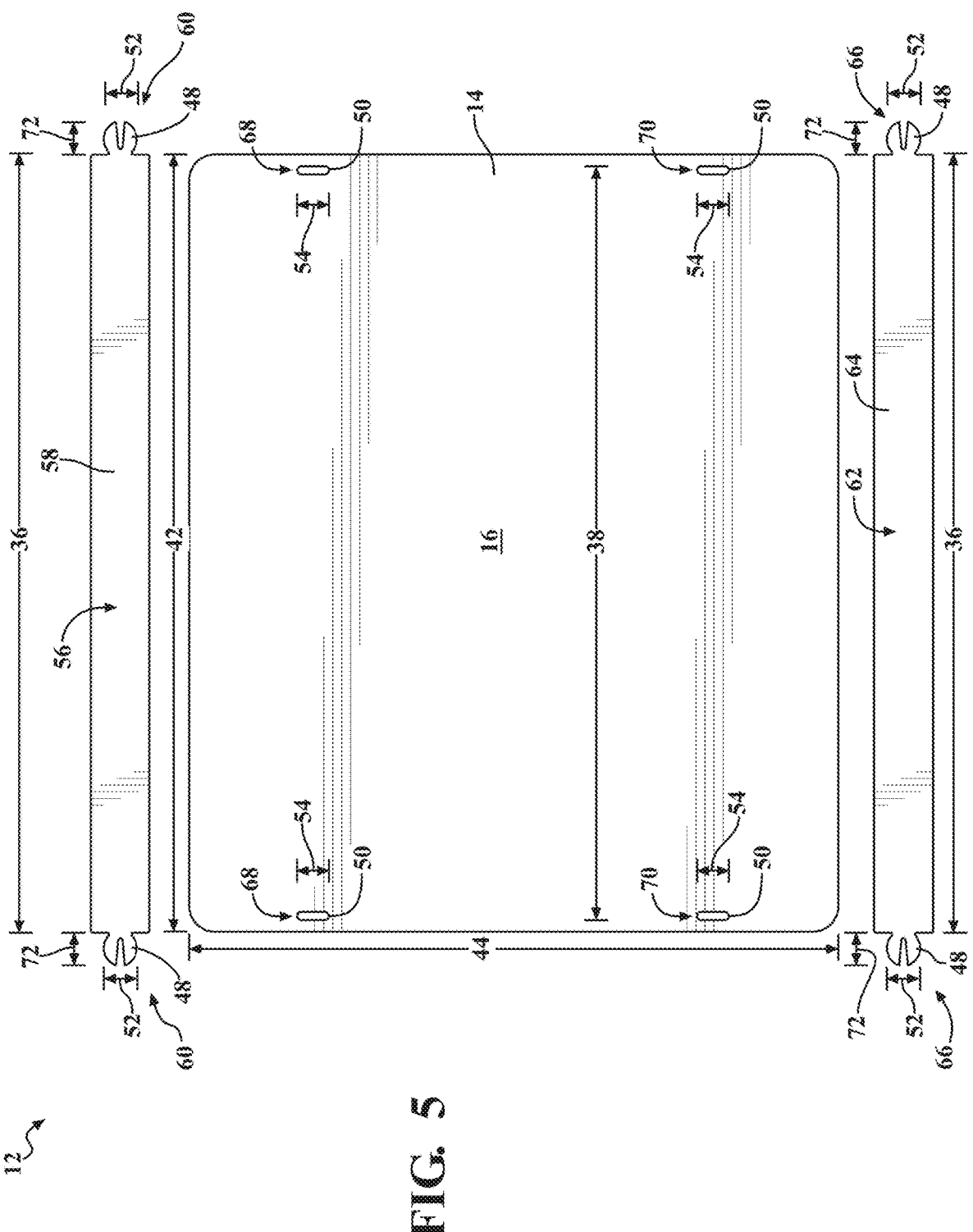
FIG. 5 is a plan view of the tray including two spacers.
Figure 8:
FIG. 8 is a perspective view of the tray partially positioned within a sterile container.

Referring to FIGS. 1, 3 and 8, the system 10 is shown including a tray 12 and a sterile container 28, which may also be referred to as a sterile pouch. The tray 12, which may also be referred to as a desiccation tray, includes a base 14 with a surface portion 16 for supporting the tissue specimen 18 and a receiver portion 20. The tray 12 also includes a spacer 22 (may also be referred to as a bridge spacer) with a body portion 24 and a securing portion 26 engaging the receiver portion 20 of the base 14 to position the body portion 24 above the surface portion 16 of the base 14. The tray 12 may include any number of spacers as desired. One spacer is shown in FIGS. 1-3 and two spacers are shown in FIGS. 4-5. The sterile container 28 includes a top 30 and a bottom 32 defining a cavity 34 such that the body portion 24 of the spacer 22 engages the top 30 of the sterile container 28 to elevate the top 30 of the sterile container 28 away from the surface portion 16 of the base 14 for protecting the tissue specimen 18 from contamination.

The base 14 of the tray 12 can be of any suitable shape, size or configuration. For example, the base 14 of the tray 12 may be circular, rectangular, or may be square depending on the specific application and/or the size of the tissue specimen 18 to be placed onto the base 14 by the user. The base 14 may be made of a flexible material but may also be more rigid depending on the specific application. Similarly, the spacer 22 of the tray 12 may have any suitable shape, size or configuration. For example, the body portion 24 of the spacer 22 may be narrower or wider than shown or may be thinner or thicker to tune the size and flexibility relative to the base 14 of the tray 12. Preferably the tray 12 and spacers 22 are formed of a common material suitable for medical use. It is also contemplated that the tray 12 and spacers 22 could be formed of different materials. One example of a suitable material is FDA grade polypropylene.

The securing portion 26 of the spacer 22 is engaged with the receiver portion 20 of the base 14 so that the body portion 24 of the spacer 22 is elevated above the surface portion 16 of the base 14. If a container is used, the body portion 24 being elevated above the surface portion 16 of the base 14 helps ensure that the top 30 of the sterile container 28 does not come into contact with the tissue specimen 18, which can be seen in FIG. 8. The body portion 24 of the spacer 22 engages the top 30 of the sterile container 28 to prevent the top 30 of the sterile container 28 from contacting the tissue specimen 18 as the tray 12 is positioned inside the sterile container 28. In other words, the body portion 24 of the spacer 22 extends upwards relative to the surface portion 16 of the base 14 when the securing portion 26 of the spacer 22 mounts to the receiver portion 20 of the base 14.

Figure 9:
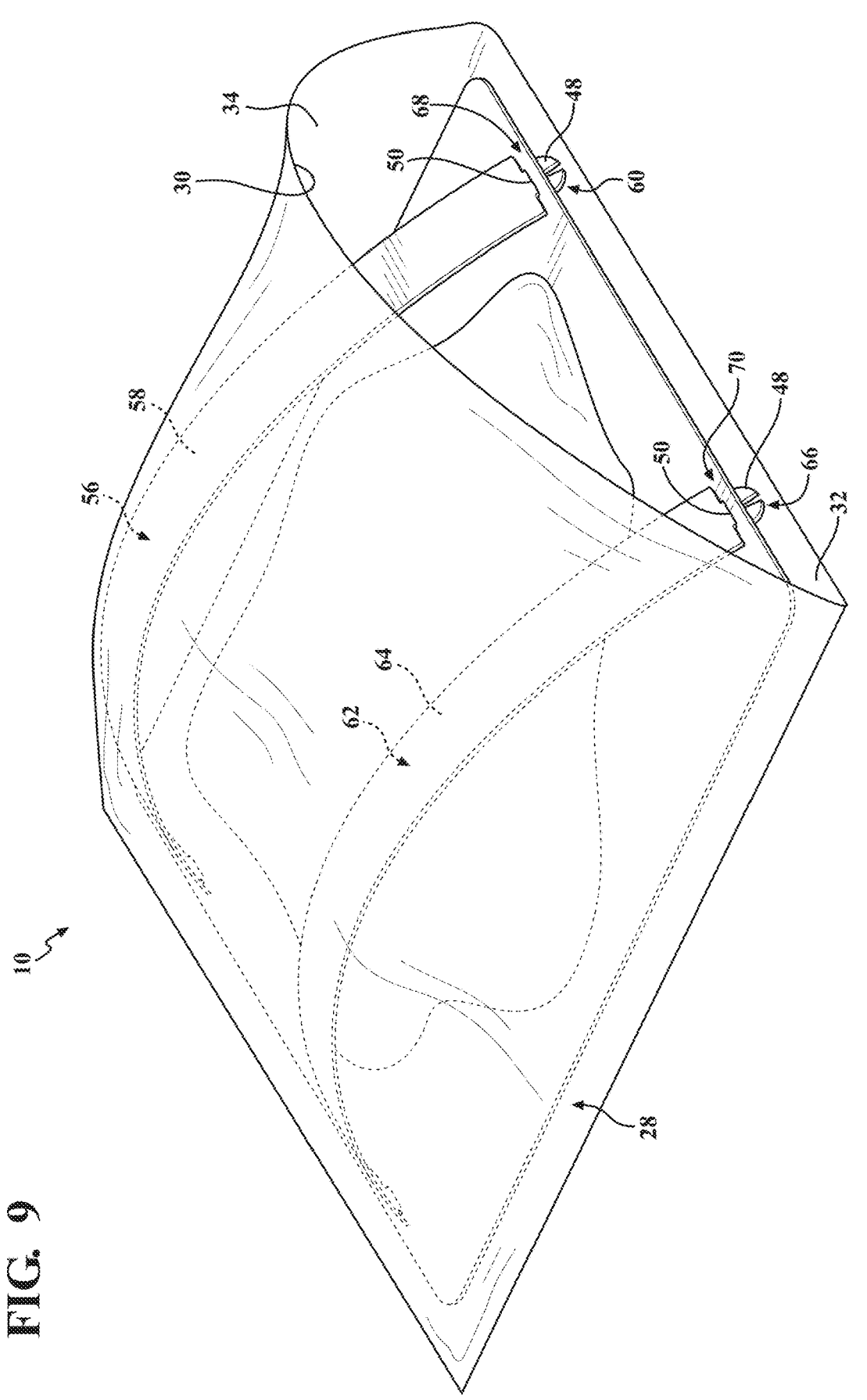
FIG. 9 is a perspective view of the tray with two spacers positioned within the sterile container.

As shown in the alternative embodiment of FIGS. 4-5 and 9, the tray 12 may include a plurality of spacers, such as two spacers, which is shown in FIG. 4. The tray 12 may include a first spacer 56 having a first body portion 58 and a first securing portion 60, and may also include a second spacer 62 having a second body portion 64 and a second securing portion 66. Each of the first and second body portions 58, 64 of the first and second spacers 56, 62 engage the top 30 of the sterile container 28 to prevent the sterile container 28 from contacting the tissue specimen 18, which is shown in FIG. 9. The tray 12 including the first and second spacers 56, 64 may be preferable if the size of the base 14 of the tray 12 is large and/or the size of the tissue specimen 18 is large.

The tray 12 allows for the tissue specimen 18 to be exposed to the air, which may help preserve the tissue specimen 18 for later use. The securing portion 26 of the spacer 22 is engaged to the receiver portion 20 of the base 14 such that at least a section of the surface portion 16 of the base 14 is extends beyond a width of the spacer 22. In other words, the size of the section of the surface portion 16 that extends beyond the spacer 22 depends on the width of the spacer 22. The section of the body portion 24 that is continuously exposed decreases as the width of the spacer 22 increases. As shown in FIG. 1, the surface portion 16 supporting the tissue specimen 18 extends beyond the size of the spacer 22 engaged to the base 14 of the tray 12. This may help in preserving and/or preparing the tissue specimen 18 prior to placing the tray 12 inside the sterile container 28. For example, the tissue specimen 18 may require to be dehydrated prior to storing the tissue specimen 18 in the sterile container 28. The tissue being continuously exposed may help air reach the tissue specimen 18 to facilitate dehydration, as an example. This is in contrast to a conventional lid that fully encapsulates the tissue, which could impede the dehydration process.

The dimensions of the base 14 and the spacer 22 help facilitate the body portion 24 of the spacer 22 engaging and elevating the top 30 of the sterile container 28 away from the surface portion 16 of the base 14. As shown in FIG. 3, the securing portion 26 of the spacer 22 may include two spaced apart securing portions 26 at each end of the body portion 24 of the spacer 22 defining a spacer length 36. Similarly, the receiver portion 20 of the base 14 may include two spaced apart receiver portions defining a receiver length 38. The spacer length 36 is preferably greater than the receiver length 38, which facilitates the body portion 24 elevating above the surface portion 16 of the base 14 once the spacer 22 is engaged to the base 14 of the tray 12. In order for the spacer length 36 to fit within the receiver length 38, it is preferable that the body portion 24 of the spacer 22 be flexible such that the body portion 24 is bent when the spacer 22 is engaged with the base 14 to position the body portion 24 within the receiver length 38. Additionally, the base 14 includes a perimeter defining a length 42 and a width 44. The receiver portions 20 of the base 14 are spaced apart from the perimeter such that receiver length 38 is less than at least one of the length 42 or width 44 of the base 14. In other words, the receiver portions 20 are positioned away from the perimeter toward the center of the surface portion 16 away from the edges of the base 14 of the tray 12. It is to be appreciated that the receiver portions 20 can be in any suitable location. The specifics of how the securing portion 26 of the spacer 22 engages with the receiver portion 20 of the base 14 is explained in greater detail below.

The securing portion 26 of the spacer 22 may engage the receiver portion 20 of the base 14 by fixedly mounting. The securing portion 26 of the spacer 22 may be defined as or may include a retention member 46 (shown in FIGS. 1-3) at each end of the body portion 24 to fixedly mount the spacer 22 to the base 14. The retention member 46 is shaped in a way so that once it is mounted to the receiver portion 20, it remains mounted, which may allow the base 14 and the spacer 22 to be transported as a unitary unit. The mounting is preferably not permanent and the securing portions 26 of the spacer 22 may be disengaged from the receiver portions 20 of the base 14, if desired.

The securing portion 26 of the spacer 22 may also engage with the receiver portion 20 by the securing portion 26 including projections 48 (may also be referred to as spacer hooks) and the receiver portion 20 including slots 50 (may also be referred to as receivers). The securing portion 26 may include two spaced apart securing portions with each securing portion having a projection 48 and the receiver portion 20 may include two spaced apart receiver portions with each receiver portion 20 including slots 50. The projections 48 of the securing portion 26 mount to the slots 50 of the receiver portion 20. Each securing portion 26 may include the projection 48 having a projection width 52 and each receiver portion 20 may include the slot 50 having a slot width 54. The progression of each projection 48 mounting to the corresponding slot 50 is shown in FIGS. 6A-6D. The projection width 52 is greater than the slot width 54 to facilitate the projections 48 interlockingly engaging the corresponding slots 50. In other words, each projection 48 is wider than each corresponding slot 50 so that when the projection 48 is engaged into each slot 50, the projection 48 effectively snaps into place. Although each engagement between the projection 48 and the corresponding slot 50 is preferably not permanent, the engagement is such that the spacer 22 may support the weight of both the base 14 and the tissue specimen 18. This may be advantageous to allow the user to lift the tray 12 along with the tissue specimen 18 by holding the body portion 24 of the spacer 22. Stated another way, the securing portion 26 of the spacer 22 engages the receiver portion 20 of the base 14 such that the spacer 22 and the base 14 are mounted together to be transported as a unitary unit. It is to be appreciated that the securing and receiver portion 26, 20 may be of any suitable design or configuration that may be permanent or disengageable, and/or may mount or simply abut.

Figure 6A:
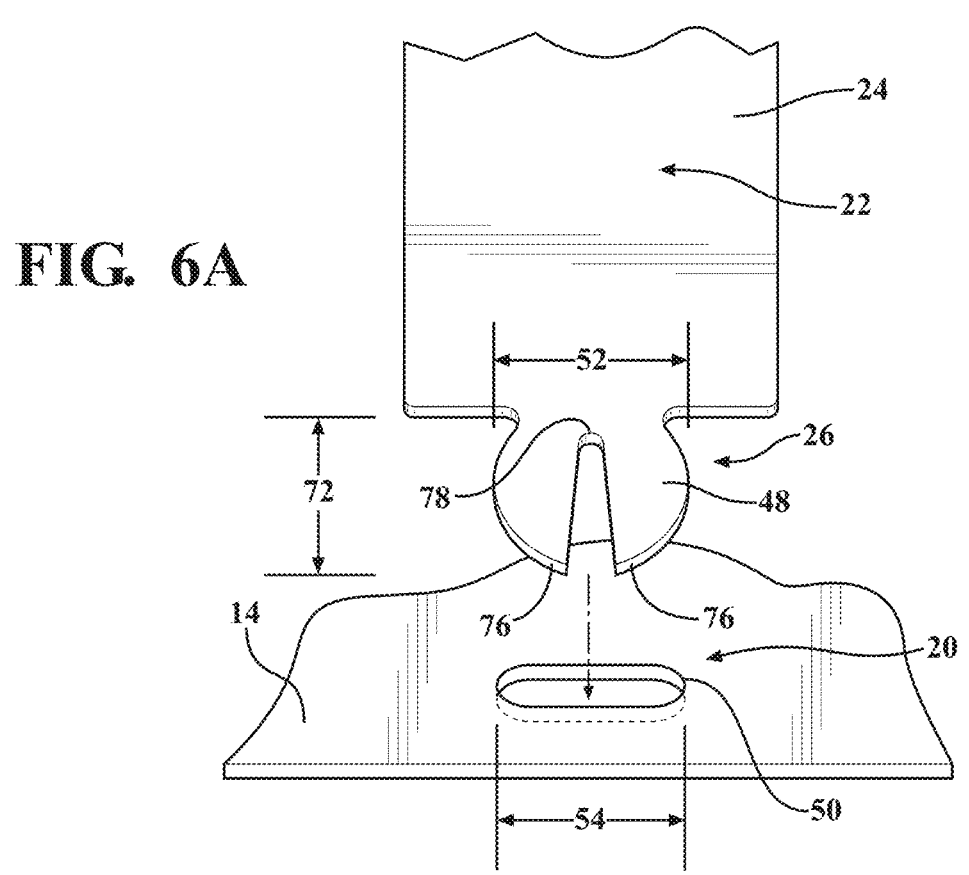
FIGS. 6A-6D are a progression of views showing a securing portion of the spacer engaging a receiver portion of the base of the tray.
Figure 6B:
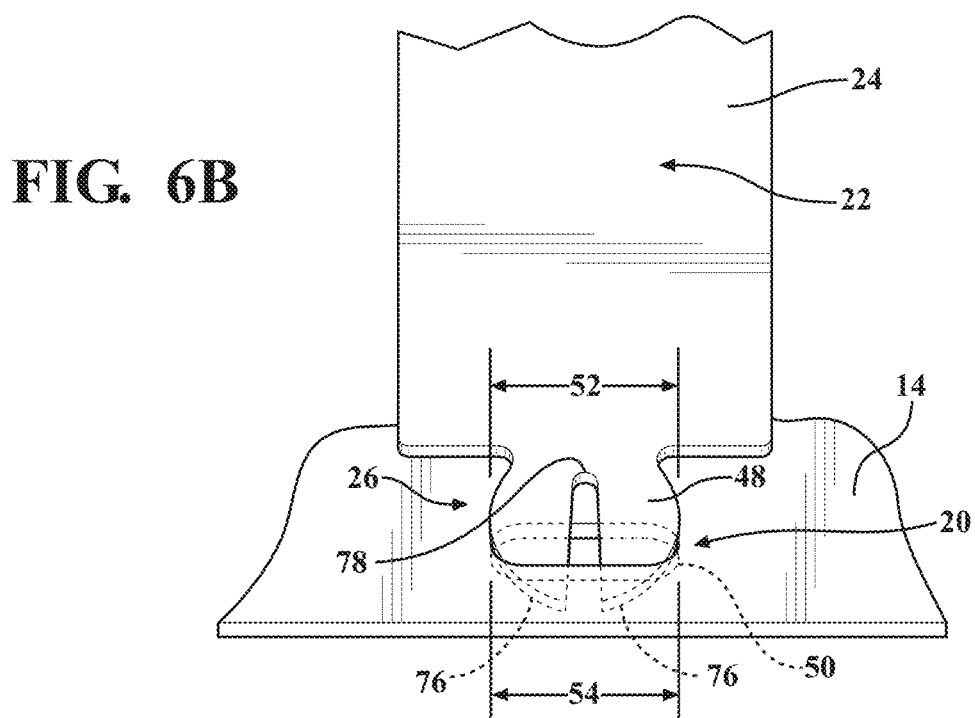
Figure 6C:
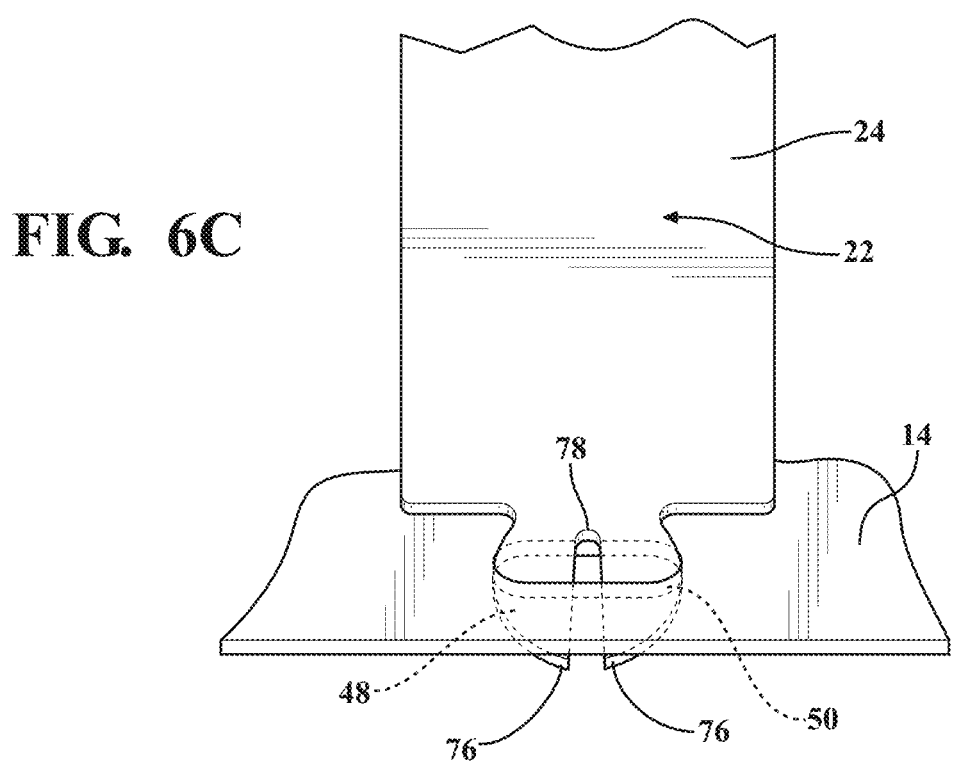
Figure 6D:
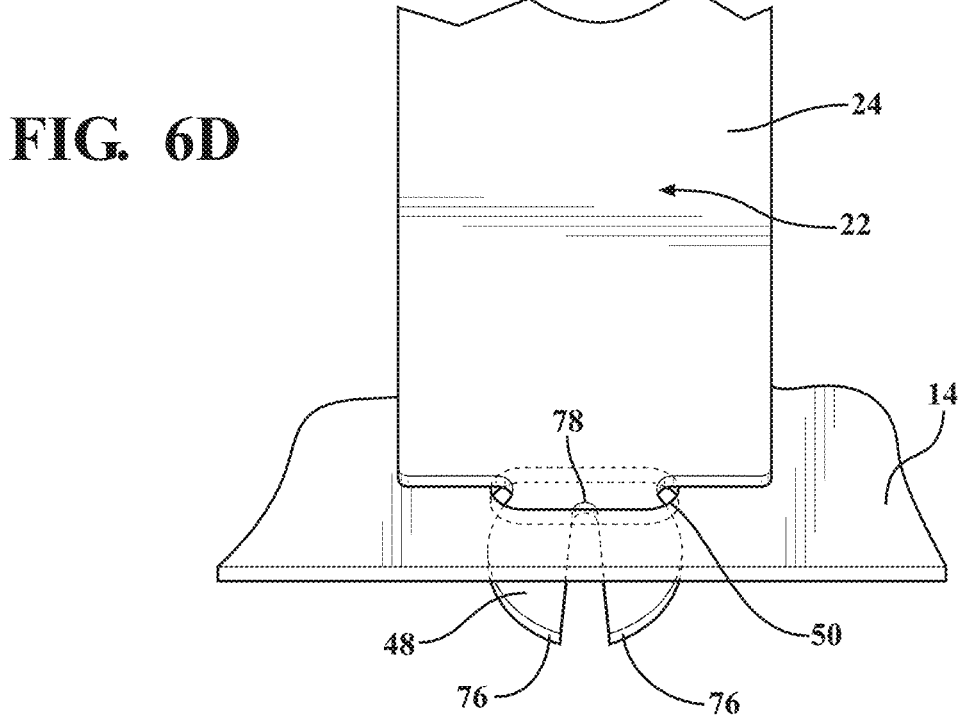
Figure 7:
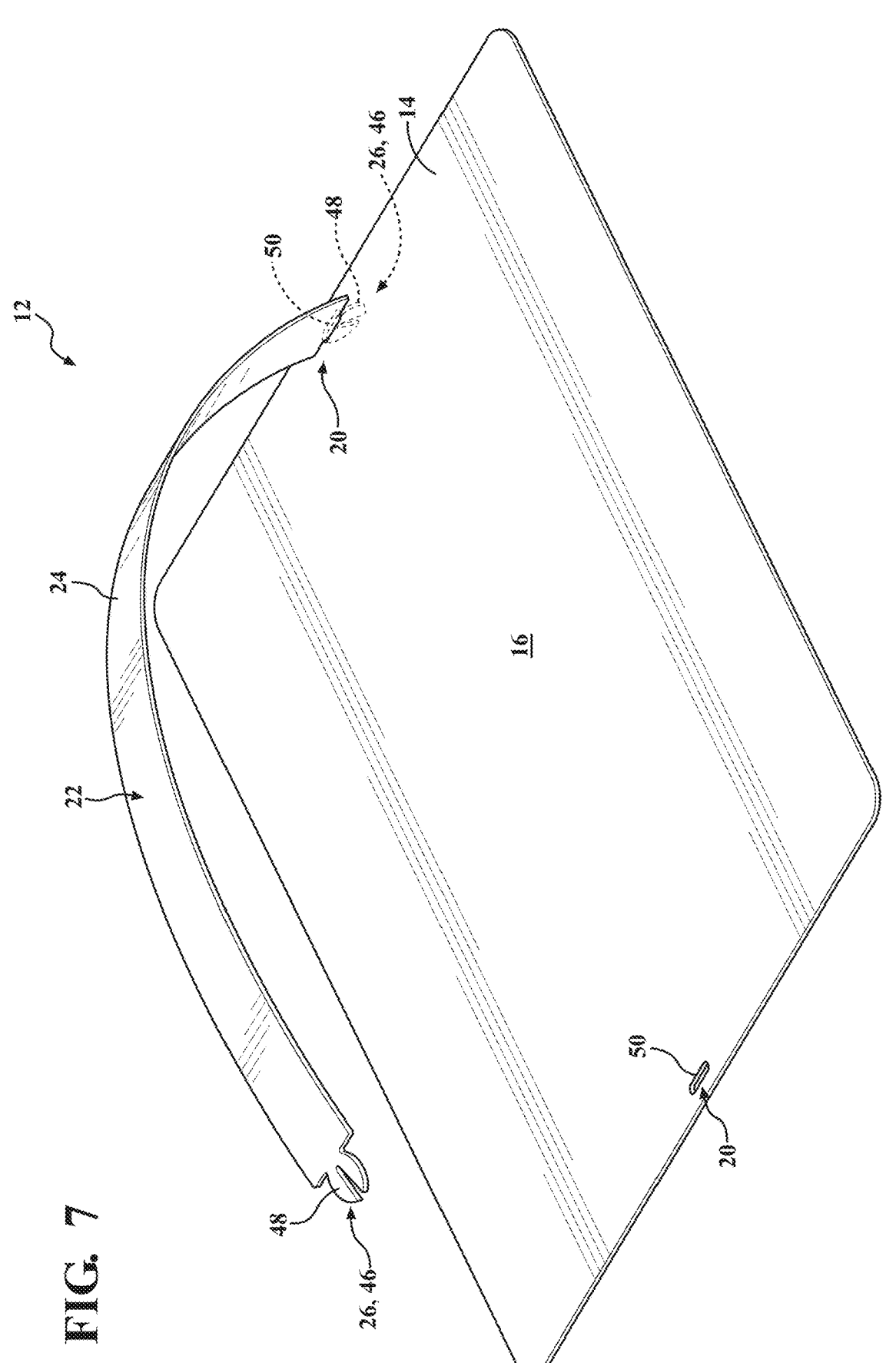
FIG. 7 is a perspective view of the tray the spacer partially engaged with the base of the tray.

The projections 48 as shown each include a projection length 72 and also each include fingers 76 (shown in FIG. 6A-6D) that extend away from the ends of the body portion 24 of the spacer 22. The fingers 76, which may also be referred to as claws or pinchers, also have a slit 78 between them that facilitates the fingers 76 to stay separated to help maintain the projection width 52. As shown in FIG. 6D, once the projection 48 is engaged into the slot 50, the fingers 76 of each projection 48 penetrate the base 14 of the tray 12 through each slot 50. When the spacer 22 is fully engaged with the base 14, the base 14 of the tray 12 rests on the fingers 76 of each projection 48. It should be appreciated that the base 14 and/or projections 48 could be configured differently such that each projection 48 does not extend beyond the base 14 of the tray 12.

The tray 12 allows a user to place the tissue specimen 18 onto the base 14 of the tray 12. The tray also allows a user to secure the spacer 22 onto the base 14 such that a portion of the spacer 22 is positioned above the base 14, which may be further defined as mounting the securing portion 26 to the slot 50 of the receiver portion 20 of the base 14. The tray may also be positioned into the sterile container 28 such that the spacer 22 elevates the sterile container 28 away from the base 14 of the tray 12 to protect the tissue specimen 18 from contamination, which may be further defined as the body portion 24 of the spacer 22 engaging and elevating the top 30 of the sterile container 28 to protect the tissue specimen 18 from contamination.

Figure 10:
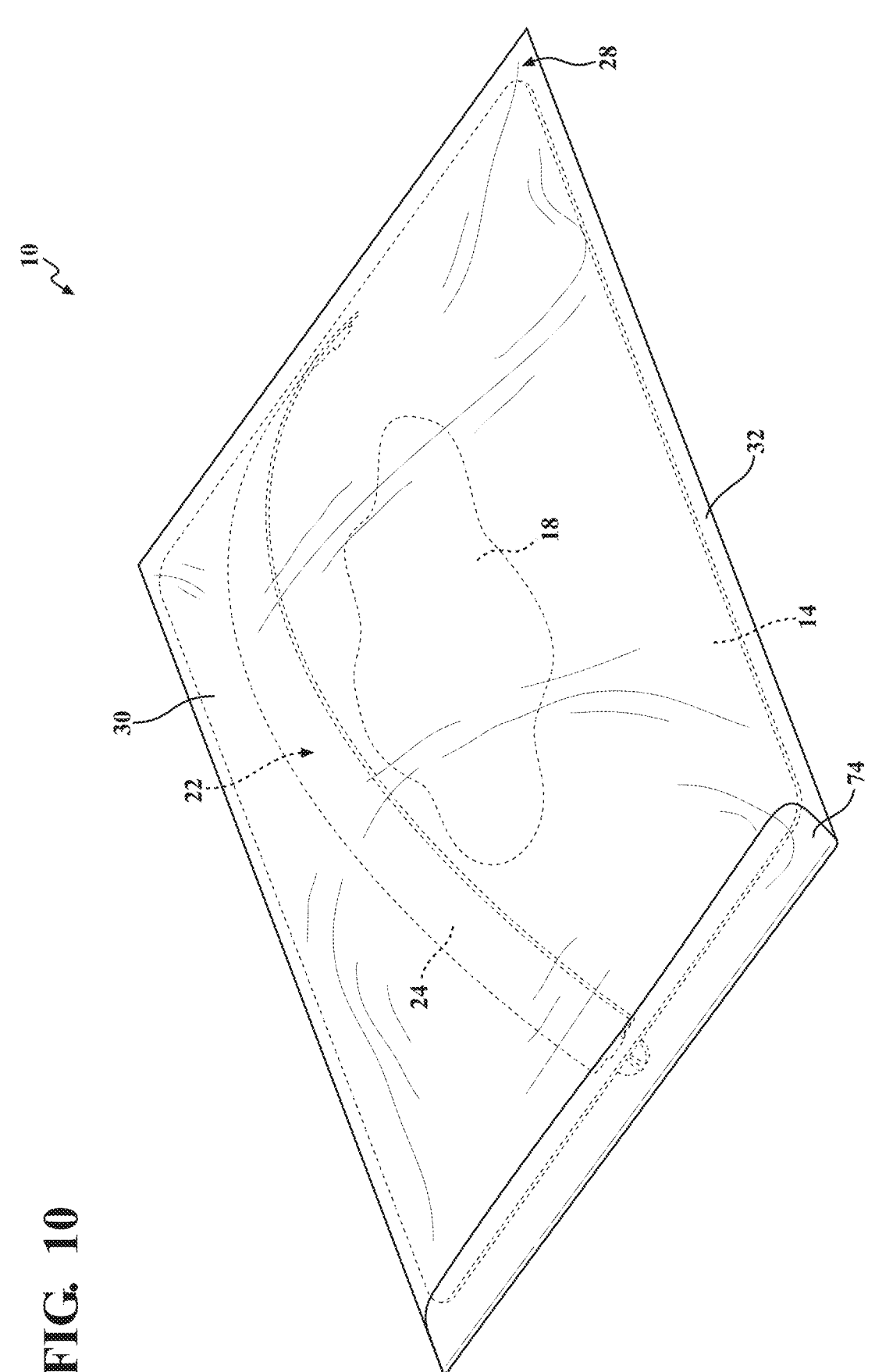
FIG. 10 is a perspective view of the tray positioned within the sterile container.

Once the tray is fully inside the sterile container 28, the sterile container 28 may be closed using a closing mechanism 74, which is shown in FIGS. 8 and 10. The closing mechanism 74 as shown is a flap of the sterile container 28 that is underneath the tray 12 as it is slid into the sterile container 28. The closing mechanism 74 is flipped over, which can seal the sterile container 28 so that the system 10 may be stored while the tissue specimen 18 retains its sterility.

An exemplary embodiment of the system 10 for protecting the tissue specimen 18 is shown. However, the embodiments discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

The invention claimed is:

1. A system for protecting a tissue specimen, said system comprising:
  a tray having:
    a base with a surface portion for supporting the tissue specimen and a receiver portion, and
    a spacer with a body portion and a securing portion engaging said receiver portion of said base to position said body portion above said surface portion of said base; and
  a sterile container having a top and a bottom defining a cavity with said tray positionable within said cavity such that said body portion of said spacer engages said top of said sterile container to elevate said top of said sterile container away from said surface portion of said base for protecting the tissue specimen from contamination
  wherein said securing portion includes two spaced apart securing portions with one at each end of said body portion defining a spacer length and wherein said receiver portion includes two spaced apart receiver portions defining a receiver length and wherein said spacer length is greater than said receiver length.

2. The system of claim 1, wherein said base has a perimeter defining a length and a width, and said receiver portions are spaced from said perimeter such that said receiver length is less than at least one of said length and said width of said base.

3. The system of claim 1, wherein said body portion of said spacer is flexible such that said body portion is bent when said spacer is engaged with said base to position said body portion within said receiver length.

4. The system of claim 1, wherein said securing portion includes a retention member at each end of said body portion of said spacer to fixedly mount said spacer to said base.

5. The system of claim 1, wherein said body portion of said spacer extends upwards relative to said surface portion of said base when said securing portion of said spacer mounts to said receiver portion of said base.

6. The system of claim 1, wherein said securing portion of said spacer engages said receiver portion of said base such that said spacer and said base are mounted together and can be transported as a unitary unit.

7. A system for protecting a tissue specimen, said system comprising:
  a tray having:
    a base with a surface portion for supporting the tissue specimen and a receiver portion, and
    a spacer with a body portion and a securing portion engaging said receiver portion of said base to position said body portion above said surface portion of said base; and
  a sterile container having a top and a bottom defining a cavity with said tray positionable within said cavity such that said body portion of said spacer engages said top of said sterile container to elevate said top of said sterile container away from said surface portion of said base for protecting the tissue specimen from contamination;
  wherein said securing portion of said spacer includes two spaced apart securing portions with each of said securing portions having a projection and said receiver portion of said base includes two spaced apart receiver portions with said receiver portions including slots with said projections of said securing portions mounting to said slots of said receiver portions.

8. The system of claim 7, wherein a section of said surface portion of said base extends beyond a width of said spacer when said securing portion of said spacer engages said receiver portion of said base.

9. The system of claim 7, wherein each of said projections has a projection width and each of said slots has a slot width and wherein said projection width is greater than said slot width such that each of said projections interlockingly engage a corresponding slot for said spacer to support a weight of both of said base and the tissue specimen.

10. A method of protecting a tissue specimen using a tray having a base and a spacer, and a sterile container, said method comprising the steps of:
  placing the tissue specimen onto the base;
  securing the spacer onto the base such that a portion of the spacer is positioned above the base; and
  positioning the tray into the sterile container such that the spacer elevates the sterile container away from the base of the tray to protect the tissue specimen from contamination;
  wherein said base includes a slot and said spacer includes a securing portion; and
  wherein the step of securing the spacer is further defined as mounting the securing portion to the slot.

11. The method of claim 10, wherein said spacer includes a body portion and said sterile container includes a top and wherein the step of positioning the tray into the sterile container is further defined as the body portion of the spacer engaging and elevating the top of the sterile container to protect the tissue specimen from contamination.

12. The method of claim 10, wherein said sterile container includes a closing mechanism and further including the step of closing the sterile container using the closing mechanism after positioning the tray into the sterile container.

13. A tray for use with a sterile container to protect a tissue specimen, said tray comprising:

a base with a surface portion and a receiver portion; and a spacer with a body portion and a securing portion engaging said receiver portion of said base to position said body portion above said surface portion of said base; and wherein said body portion of said spacer remains positioned above said surface portion of said base for continuously protecting the tissue specimen as said tray is positioned within the sterile container wherein said securing portion includes two spaced apart securing portions with one at each end of said body portion defining a spacer length and wherein said receiver portion includes two spaced apart receiver portions defining a receiver length and wherein said spacer length is greater than said receiver length.

14. The tray of claim 13, wherein said base has a perimeter defining a length and a width, and said receiver portions are spaced from said perimeter such that said receiver length is less than at least one of said length and said width of said base.

15. The tray of claim 13, wherein said body portion of said spacer is flexible such that said body portion is bent when said spacer is engaged with said base to position said body portion within said receiver length.

16. The tray of claim 13, wherein said securing portion of said spacer engages said receiver portion of said base such that said spacer and said base are mounted together and can be transported as a unitary unit.

17. A tray for use with a sterile container to protect a tissue specimen, said tray comprising:

a base with a surface portion and a receiver portion; and a spacer with a body portion and a securing portion engaging said receiver portion of said base to position said body portion above said surface portion of said base; and wherein said body portion of said spacer remains positioned above said surface portion of said base for continuously protecting the tissue specimen as said tray is positioned within the sterile container; and wherein said receiver portion is defined as a slot and said securing portion is defined as a retention member engaging said slot to mount said spacer to said base.

18. The tray of claim 17, wherein a section of said surface portion of said base extends beyond a width of said spacer when said securing portion of said spacer engages said receiver portion of said base.

19. A tray for use with a sterile container to protect a tissue specimen, said tray comprising:

a base with a surface portion and a receiver portion; and a spacer with a body portion and a securing portion engaging said receiver portion of said base to position said body portion above said surface portion of said base;

wherein said body portion of said spacer remains positioned above said surface portion of said base for continuously protecting the tissue specimen as said tray is positioned within the sterile container; and wherein said spacer is further defined as a first spacer having a first body portion and a first securing portion and further including a second spacer having a second body portion and a second securing portion, and wherein said receiver portion of said base is further defined as a first receiver portion and further including a second receiver portion of said base such that said first securing portion of said first spacer engages said first receiver portion of said base and said second securing portion of said second spacer engages said second receiver portion of said base.

* * * * *